(12) United States Patent
Nishimura et al.

(10) Patent No.: US 10,744,659 B2
(45) Date of Patent: Aug. 18, 2020

(54) ASEPTIC WORK SYSTEM

(71) Applicant: SHIBUYA CORPORATION, Kanazawa-shi, Ishikawa (JP)

(72) Inventors: Tetsuya Nishimura, Kanazawa (JP); Kazuhito Tanimoto, Kanazawa (JP)

(73) Assignee: SHIBUYA CORPORATION, Kanazawa-Shi, Ishikawa (JP)

(*) Notice: Subject to any disclaimer, the term of this patent is extended or adjusted under 35 U.S.C. 154(b) by 113 days.

(21) Appl. No.: 16/224,061

(22) Filed: Dec. 18, 2018

(65) Prior Publication Data

US 2019/0193287 A1 Jun. 27, 2019

(30) Foreign Application Priority Data

Dec. 27, 2017 (JP) ................. 2017-252426

(51) Int. Cl.
*B25J 21/02* (2006.01)
*C12M 1/00* (2006.01)
(Continued)

(52) U.S. Cl.
CPC .............. *B25J 21/02* (2013.01); *B25J 21/005* (2013.01); *C12M 23/40* (2013.01); *C12M 23/44* (2013.01);
(Continued)

(58) Field of Classification Search
CPC ........ B25J 21/02; B25J 21/005; C12M 23/40; C12M 23/44; C12M 23/52; C12M 37/04; C12M 37/00; C12M 41/14; B01L 1/02; B01L 1/00; B01L 2200/0689; B01L 2300/043; B01L 2300/046; G21F 7/005; G21F 7/047; H01L 21/67772; H01L 21/67775; H01L 21/67379; A47B 47/0091; A47B 81/00; B65D 51/28; F25D 23/025; F25D 2323/023
(Continued)

(56) References Cited

U.S. PATENT DOCUMENTS 4,111,753 A * 9/1978 Folsom ..................... B01L 1/00
                                                                    435/3
4,162,196 A * 7/1979 Folsom ..................... B01L 1/02
                                                                    435/304.1
(Continued)

FOREIGN PATENT DOCUMENTS

| CA | 2972000 | * 12/2017 |
| JP | 2015104358 | * 6/2015 |
| JP | 2017-169502 A | 9/2017 |

*Primary Examiner* — Janet M Wilkens
(74) *Attorney, Agent, or Firm* — Flynn Thiel, P.C.

(57) ABSTRACT

A main isolator 2 (main aseptic device) includes a main connection part 6 having an opening O through which a work space W is externally opened, and an internal opening and closing member 22 configured to open and close an internal opening 21a of the main connection part 6 on the work space W side. A manual incubator 3 (first auxiliary aseptic device) includes a first auxiliary connection part 7 connectable with the main connection part 6 of the main isolator 2, and an automatic incubator 4 and a housing container 5 (second auxiliary aseptic devices) each include a second auxiliary connection part 8 smaller than the first auxiliary connection part 7. In addition, an external blockage member 9 configured to externally block the opening O of the main connection part 6 is provided.

7 Claims, 7 Drawing Sheets

(51) Int. Cl.
*B25J 21/00* (2006.01)
*C12M 1/12* (2006.01)
*C12M 3/00* (2006.01)

(52) U.S. Cl.
CPC ............ *C12M 23/52* (2013.01); *C12M 37/04* (2013.01); *C12M 41/14* (2013.01); *C12M 37/00* (2013.01)

(58) Field of Classification Search
USPC ..................................................... 312/1, 292
See application file for complete search history.

(56) References Cited

U.S. PATENT DOCUMENTS

| | | | | |
|---|---|---|---|---|
| 5,139,459 A * | 8/1992 | Takahashi | ......... | H01L 21/67126 454/187 |
| 5,219,215 A * | 6/1993 | Akagawa | ................. | B01L 9/02 312/1 |
| 5,425,793 A * | 6/1995 | Mori | ................. | B01D 46/0013 55/385.2 |
| 5,567,025 A * | 10/1996 | Haag, III | ................. | B01L 1/02 220/377 |
| 5,683,030 A * | 11/1997 | Moore | ................. | B65F 1/0053 232/43.1 |
| 5,783,156 A * | 7/1998 | Renzi | ....................... | F26B 5/06 312/1 |
| 6,241,328 B1 * | 6/2001 | Ziff | ....................... | A61C 13/12 312/1 |
| 6,553,722 B1 * | 4/2003 | Porret | ....................... | B01L 1/02 49/507 |
| 7,322,812 B2 * | 1/2008 | Romer | ..................... | B25J 21/02 425/151 |
| 9,168,520 B2 * | 10/2015 | Armau | ..................... | B01L 1/02 |
| 9,789,480 B2 * | 10/2017 | Funazuka | ................ | B01L 1/04 |
| 10,093,892 B2 * | 10/2018 | Nishimura | .............. | A61L 2/208 |
| 10,220,382 B2 * | 3/2019 | Yamamoto | ................ | B01L 1/02 |
| 2005/0168117 A1 * | 8/2005 | Porret | ....................... | B01L 1/02 312/291 |
| 2008/0008564 A1 * | 1/2008 | Bonora | ............. | H01L 21/67775 414/217 |
| 2013/0162117 A1 * | 6/2013 | Hara | ..................... | H01L 21/67742 312/31 |
| 2013/0167442 A1 * | 7/2013 | Sacca | ..................... | G21F 7/005 49/70 |
| 2016/0339130 A1 * | 11/2016 | Shomura | ................ | C12M 41/40 |

* cited by examiner

ASEPTIC WORK SYSTEM

BACKGROUND OF THE INVENTION

Field of the Invention

The present invention relates to an aseptic work system, and particularly relates to an aseptic work system in which a main aseptic device including inside an aseptically maintained work space is detachably provided with an auxiliary aseptic device including an aseptically maintained internal space.

Description of the Related Art

In a conventionally known aseptic work system, a main aseptic device including inside an aseptically maintained work space is detachably provided with an auxiliary aseptic device including an aseptically maintained internal space, and the work space of the main aseptic device and the internal space of the auxiliary aseptic device are capable of being communicated with each other while being aseptically maintained (Japanese Patent Laid-Open No. 2017-169502).

In the above-described Japanese Patent Laid-Open No. 2017-169502, a main isolator as the main aseptic device is detachably provided with, for example, an incubator and a material installation module as the auxiliary aseptic devices. When the work space of the main isolator and each of the internal spaces of the incubator and the material installation module are communicated with each other while being aseptically maintained, a culture container in which cells are sown can be housed in the incubator, and materials such as containers and instruments used in a culture operation can be conveyed from the material installation module into the main isolator.

The above-described aseptic work system according to Japanese Patent Laid-Open No. 2017-169502 includes two kinds of auxiliary aseptic devices, namely an incubator and a material installation module, but these devices includes opening parts in sizes different from each other.

Thus, the main isolator according to Japanese Patent Laid-Open No. 2017-169502 is provided with connection ports corresponding to the incubator and the material installation module, respectively. With such a configuration, when a larger number of kinds of auxiliary aseptic devices needs to be connected, the number of connection ports needs to be increased in accordance with the number of kinds of auxiliary aseptic devices.

As a result, side wall surfaces of the main aseptic device need space for providing a plurality of connection ports in accordance with the kinds of auxiliary aseptic devices, which leads to increase in the size of the main isolator.

The present invention is intended to solve such a problem and provide an aseptic work system in which a main aseptic device can be connected with a plurality of kinds of auxiliary aseptic devices without increase in the size of the main aseptic device.

SUMMARY OF THE INVENTION

Specifically, an aseptic work system according to the invention of claim 1 is an aseptic work system in which a main aseptic device including inside an aseptically maintained work space is detachably provided with auxiliary aseptic devices each including an aseptically maintained internal space, and the work space of the main aseptic device and the internal spaces of the auxiliary aseptic devices are capable of being communicated with each other while being aseptically maintained.

The main aseptic device includes a main connection part having an opening through which the work space is externally opened, and an internal opening and closing member configured to open and close the opening of the main connection part in the work space.

The auxiliary aseptic devices are a first auxiliary aseptic device including a first auxiliary connection part connectable with the main connection part of the main aseptic device, and a second auxiliary aseptic device including a second auxiliary connection part smaller than the first auxiliary connection part.

An external blockage member configured to externally block the opening of the main connection part is provided, and the external blockage member includes a connection opening part to which the second auxiliary connection part is connectable.

According to the above-described invention, the external blockage member configured to externally block the opening of a main connection part is provided, and the external blockage member includes the connection opening part to which the second auxiliary connection part is connectable. With this configuration, the main connection part of the main aseptic device can be connected not only with the first auxiliary connection part of the first auxiliary aseptic device but also with the second auxiliary connection part of the second auxiliary aseptic device smaller than the first auxiliary connection part. This eliminates the need to provide the main aseptic device with a connection part corresponding to each auxiliary aseptic device, thereby preventing increase in the size of the main aseptic device.

BRIEF DESCRIPTION OF THE DRAWINGS

FIGS. 1A, 1B, and 1C are diagrams illustrating an isolator system according to the present embodiment.

DETAILED DESCRIPTION OF THE PREFERRED EMBODIMENT

Figure 1A:
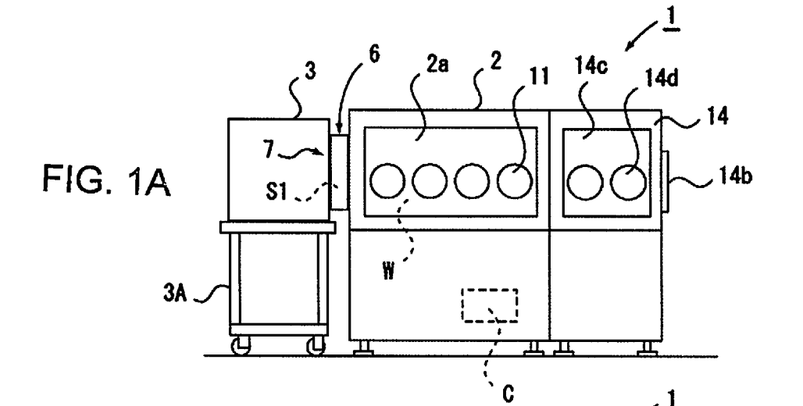
FIG. 1A illustrates a state in which a main isolator is connected with a manual incubator.
Figure 1B:
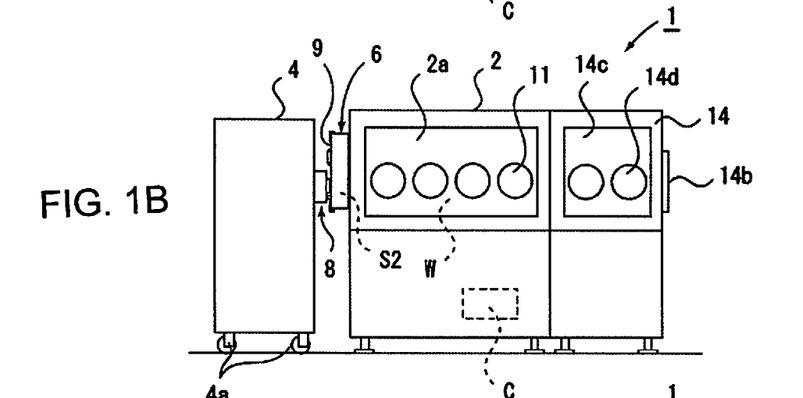
FIG. 1B illustrates a state in which the main isolator is connected with an automatic incubator.
Figure 1C:
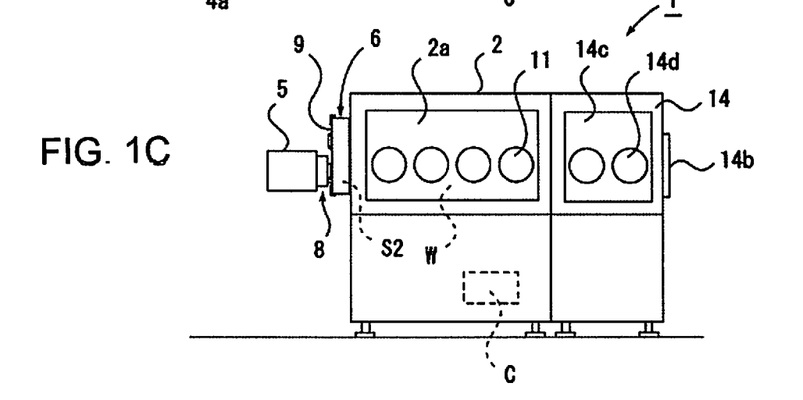
FIG. 1C illustrates a state in which the main isolator is connected with a housing container.

The following describes an embodiment with reference to the accompanying drawings. FIGS. 1A, 1B, and 1C each illustrate an isolator system 1 that includes an aseptic work system according to the present invention and in which culture work of cells or the like is performed. The isolator system 1 is provided in a work room at, for example, a culture facility.

The isolator system 1 includes a main aseptic device including inside an aseptically maintained work space W and configured to perform work necessary for culture, and an auxiliary aseptic device including an aseptically maintained internal space. The main aseptic device is a main isolator 2. The auxiliary aseptic devices are a manual incubator 3 (refer to FIG. 1A) as a first auxiliary aseptic device housing a culture container and configured to perform cell culture, an automatic incubator 4 (refer to FIG. 1B) as a second auxiliary aseptic device including an automatic housing mechanism (not illustrated) in an internal space and configured to automatically house a culture container, and a housing container 5 (refer to FIG. 1C) as another second auxiliary aseptic device capable of housing materials and wastes in an internal space.

In the aseptic work system according to the present invention, a main connection part 6 provided on the main isolator 2 as the main aseptic device can be detachably and selectively connected with a first auxiliary connection part 7 of the manual incubator 3 as the first auxiliary aseptic device, or a second auxiliary connection part 8 of each of the automatic incubator 4 and the housing container 5 as the second auxiliary aseptic devices.

Specifically, the main connection part 6 of the main isolator 2 can be directly connected with the first auxiliary connection part 7 of the manual incubator 3. Accordingly, the work space W of the main isolator 2 and the internal space of the manual incubator 3 can be communicated with each other while being aseptically maintained.

The second auxiliary connection part 8 of each of the automatic incubator 4 and the housing container 5 is smaller than the first auxiliary connection part 7. Accordingly, the main connection part 6 cannot be directly connected with the second auxiliary connection part 8.

Thus, in the present embodiment, an external blockage member 9 configured to externally block an opening O provided in the main connection part 6 is provided, and the external blockage member 9 includes a connection opening part Oc to which the second auxiliary connection part 8 is connectable. When the connection opening part Oc is connected with the second auxiliary connection part 8, the work space W of the main isolator 2 and the internal space of each of the automatic incubator 4 and the housing container 5 are communicated with each other while being aseptically maintained.

Figure 3:
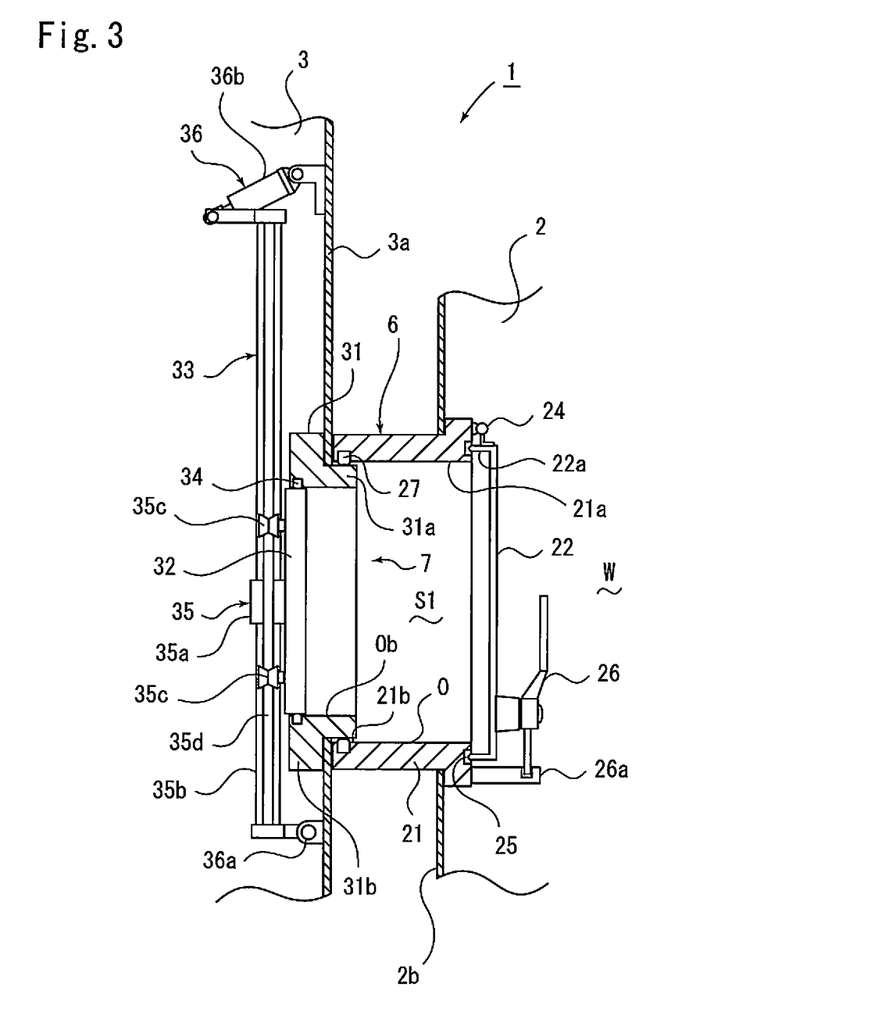
FIG. 3 is a transverse sectional view of a state in which a main connection part is connected with a first auxiliary connection part.
Figure 4:
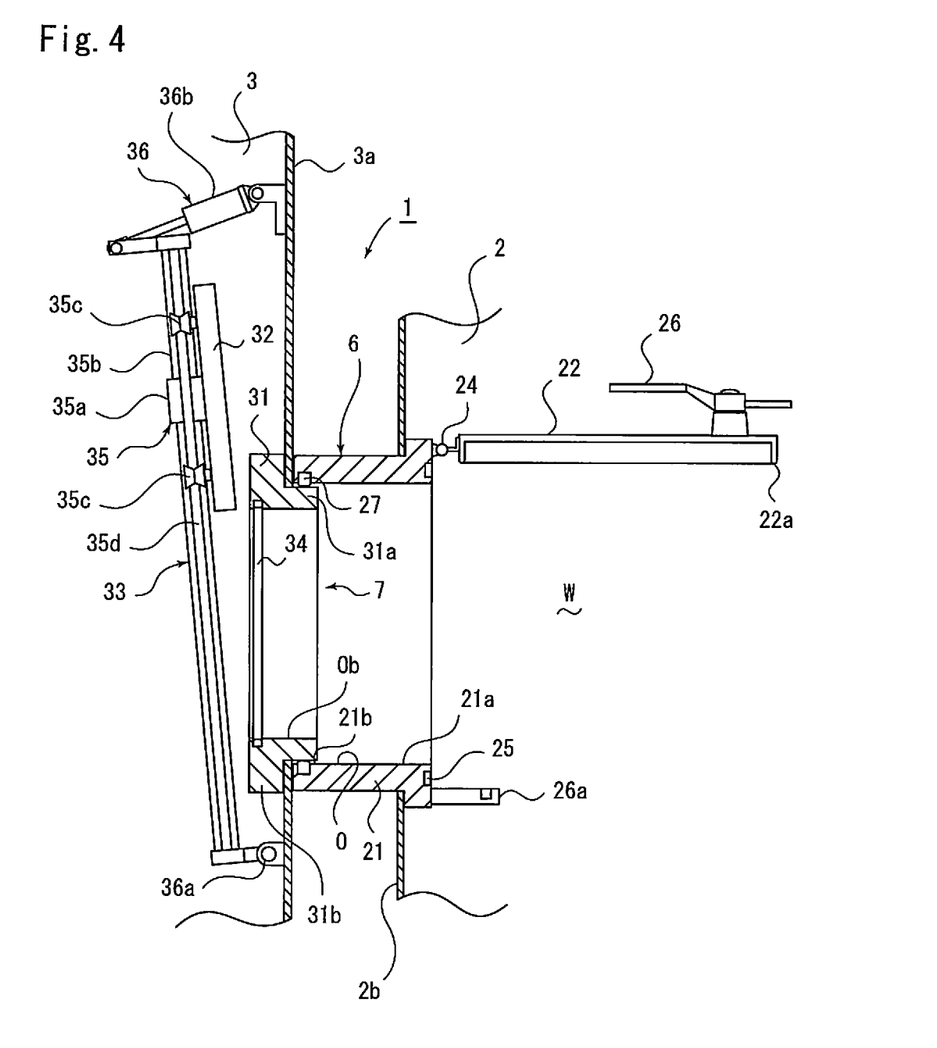
FIG. 4 is another transverse sectional view of the state in which the main connection part is connected with the first auxiliary connection part, illustrating a state in which the work space is communicated with an internal space.
Figure 5:
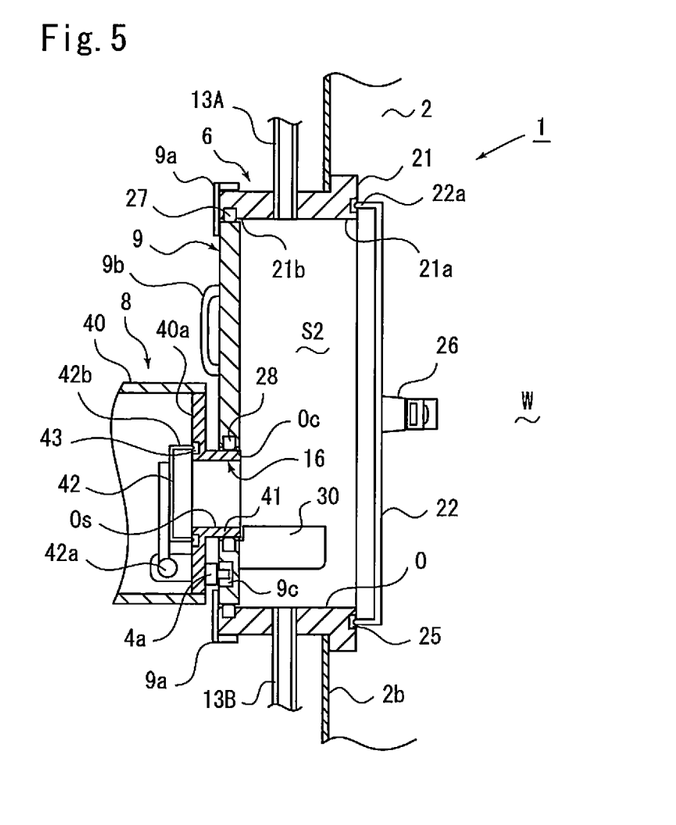
FIG. 5 is a longitudinal sectional view of a state in which the main connection part is connected with a second auxiliary connection part through an external blockage member.
Figure 6:
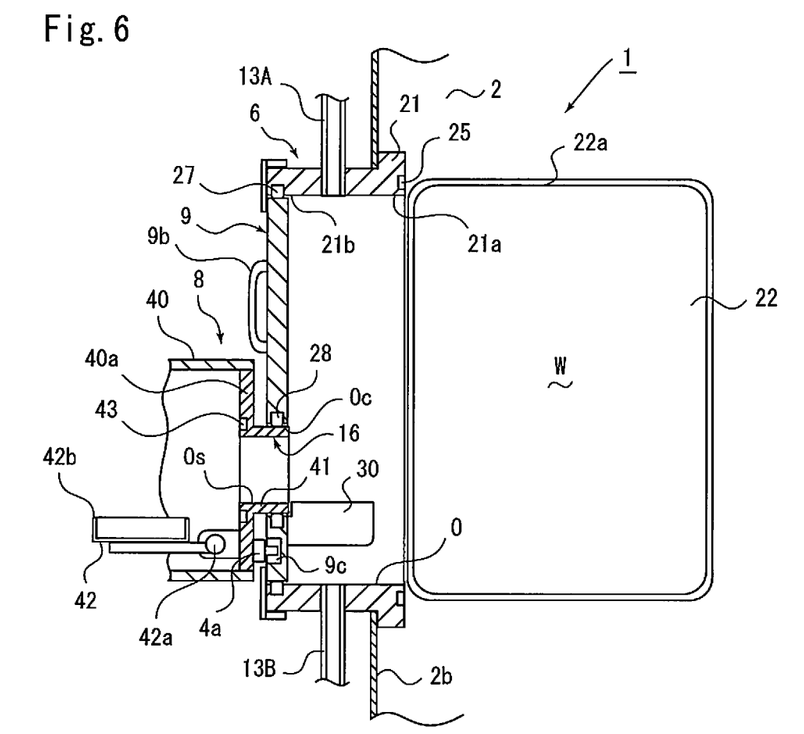
FIG. 6 is another longitudinal sectional view of the state in which the main connection part is connected with the second auxiliary connection part through the external blockage member, illustrating a state in which the work space is communicated with the internal space.

FIGS. 3 and 4 are transverse sectional views illustrating a state in which the main connection part 6 of the main isolator 2 is connected with the first auxiliary connection part 7 of the manual incubator 3. FIGS. 5 and 6 are transverse sectional views illustrating a state in which the opening O of the main connection part 6 of the main isolator 2 is blocked by the external blockage member 9 and connected with the second auxiliary connection part 8 of the automatic incubator 4 or the housing container 5.

The main isolator 2 includes an aseptic air supply means (not illustrated) to aseptically maintain the work space W inside, and a transparent window 2a positioned on the front side and provided with a glove 11 to be worn by a worker when working in the work space W.

Figure 2:
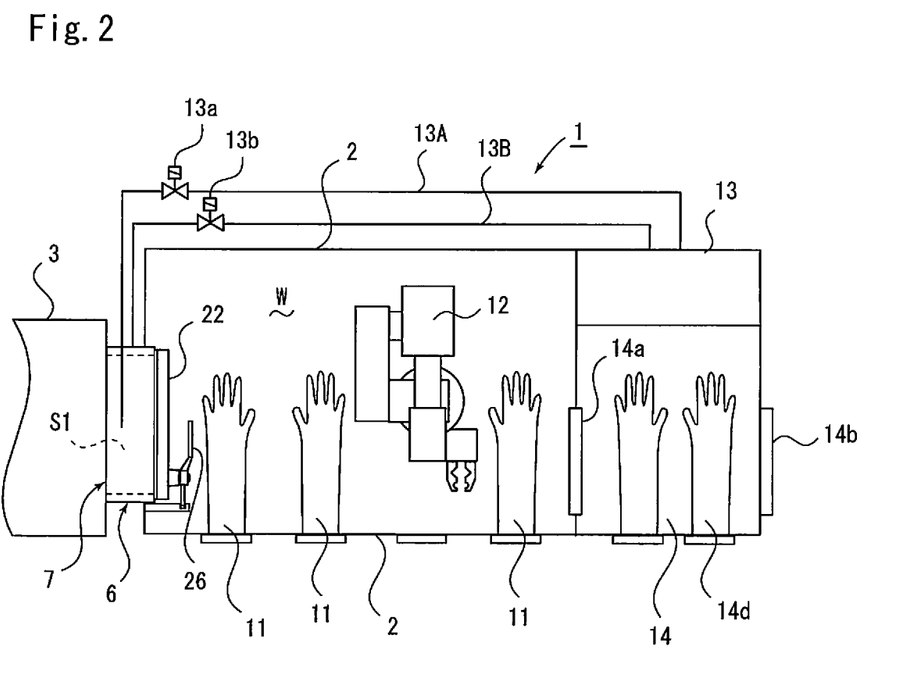
FIG. 2 is a plan view illustrating a work space of the main isolator.

FIG. 2 is a plan view illustrating the work space W inside the main isolator 2. The work space W is provided with a robot 12 including a hand and capable of automatically performing culture work at a work position set around the robot 12.

The main isolator 2 is provided with a decontamination means 13 for decontaminating the work space W and a connection space S1 or S2 formed by the main connection part 6. The decontamination means 13 decontaminates the work space W and the connection spaces S1 and S2 by filling the spaces with decontamination gas such as hydrogen peroxide steam as a decontamination medium, and performs aeration to externally discharge the filling decontamination gas after the decontamination finishes.

The main isolator 2 also includes a pass box 14 through which a material is conveyed on a sidewall opposite to a sidewall on the main connection part 6 side. The work space W of the main isolator 2 and an internal space of the pass box 14 are partitioned from each other by a door 14a.

The internal space of the pass box 14 is also partitioned from the outside by a door 14b to perform decontamination of a material or the like conveyed from the outside by using the decontamination means 13. The material conveyance work is performed through a glove 14d provided in a window 14c on the front side of the pass box 14.

Operation of the isolator system 1 thus configured is controlled by a control unit C achieved by a computer included in the main isolator 2.

The main connection part 6 provided on the main isolator 2 with reference to FIGS. 3 to 6. The main connection part 6 includes a tubular member 21 penetrating through a sidewall 2b of the main isolator 2. The work space W can be externally opened through the opening O formed inside the tubular member 21.

The main connection part 6 includes an internal opening and closing member 22 configured to open and close an internal opening 21a formed at an end part of the tubular member 21 on the work space W side, and the external blockage member 9 configured to block an outside opening 21b formed at an end part of the tubular member 21 on the outer side. In the present embodiment, the tubular member 21 is formed in a rectangular tube shape having the opening O in an elongated rectangular shape with round corners.

As illustrated in FIGS. 2, 5, and 6, the tubular member 21 is connected with a supply pipe 13A that includes a supply valve 13a and through which decontamination gas is supplied as the decontamination medium from the decontamination means 13 and with a discharge pipe 13B that includes a discharge valve 13b and through which the decontamination gas is discharged. With this configuration, the decontamination gas can be supplied into the tubular member 21.

The internal opening and closing member 22 is rotatably attached by a hinge 24 provided in the work space W. The internal opening and closing member 22 is closed in an air-tight state when an outer peripheral rim 22a of the internal opening and closing member 22 closely contacts a sealing member 25 provided around the rectangular internal opening 21a of the tubular member 21.

The internal opening and closing member 22 is provided with a lever 26 that can be operated in the work space W. The work space W is provided with a lever holder 26a with which the lever 26 is engaged to maintain the closed state of the internal opening and closing member 22. When the lever 26 is engaged with the lever holder 26a, the outer peripheral rim 22a of the internal opening and closing member 22 is pressed against the sealing member 25.

Figure 7:
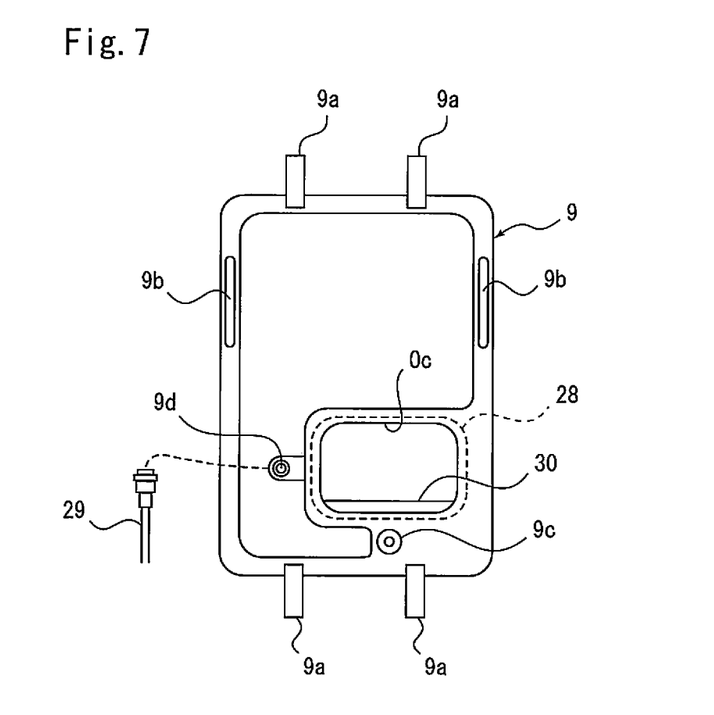
FIG. 7 is a front view of the external blockage member.

FIG. 7 illustrates a front view of the external blockage member 9. Hooks 9a to be engaged with an outer peripheral surface of the tubular member 21 are provided at upper and lower parts of the external blockage member 9. In addition, handles 9b to be held by the worker and a positioning recess 9c to be engaged with a positioning pin 4a included in a second auxiliary connection part 8 to be described later are formed at externally exposed parts of the external blockage member 9.

The external blockage member 9 is provided to be engaged with an inner peripheral surface of the rectangular outside opening 21b of the tubular member 21 in the main connection part 6. The inner peripheral surface of the outside opening 21b of the tubular member 21 is provided with an expansion seal 27 as a sealing means connected with the air supply means (not illustrated).

When expanding, the expansion seal 27 closely contacts an outer peripheral surface of the external blockage member 9, thereby sealing a gap generated where the tubular member 21 and the external blockage member 9 are engaged with each other.

The connection opening part Oc is provided at a necessary place of the external blockage member 9 and connected with the second auxiliary connection part 8 of each of the automatic incubator 4 and the housing container 5.

An expansion seal 28 is provided on an inner peripheral surface of the connection opening part Oc, and communicated with a connection port 9d provided on the front side of the external blockage member 9 through a path (not illustrated) provided inside the external blockage member 9.

The connection port 9d is connectable with an air supply hose 29 connected with the air supply means (not illustrated). The expansion seal 28 is expanded by air from the air supply means to seal the gap between the expansion seal 28 and the second auxiliary connection part 8 inserted in the connection opening part Oc.

In addition, a placement table 30 is provided adjacent below the connection opening part Oc on the back surface side of the external blockage member 9. When a culture container is transferred between the main isolator 2 and the automatic incubator 4, the culture container is temporarily placed on the placement table 30.

The manual incubator 3 as the first auxiliary aseptic device has an internal space aseptically maintained in environment preferable for cell culture by an environment maintaining means. The manual incubator 3 includes inside a rack or the like on which a culture container is to be placed. The manual incubator 3 is movable on a truck 3A.

The first auxiliary connection part 7 provided on the manual incubator 3 includes a first annular member 31 formed in an elongated rectangular shape and internally and externally provided on a front surface 3a of the manual incubator 3. The inner side of the first annular member 31 is formed as an opening Ob through which the internal space of the manual incubator 3 is externally opened.

An externally protruding outside portion 31a of the first annular member 31 can be engaged with the outside opening 21b of the tubular member 21 included in the main connection part 6 provided on the main isolator 2.

When the expansion seal 27 provided on the tubular member 21 is expanded while the outside portion 31a of the first annular member 31 is inserted into the outside opening 21b of the tubular member 21 provided on the main isolator 2, the expansion seal 27 closely contacts an outer peripheral surface of the outside portion 31a, thereby sealing a gap generated where the tubular member 21 and the first annular member 31 are engaged with each other.

An inside portion 31b pointing to an internal space of the first annular member 31 is closed by a first closing member 32. The first closing member 32 is opened and closed by an opening and closing means 33 provided in the internal space of the manual incubator 3.

The first closing member 32 can be engaged with an inner peripheral surface of the inside portion 31b of the first annular member 31. The inner peripheral surface of the inside portion 31b is provided with an expansion seal 34 as a sealing means connected with the air supply means (not illustrated).

With this configuration, when the expansion seal 34 is expanded while the first closing member 32 is engaged with the inside portion 31b of the first annular member 31, the expansion seal 34 closely contacts an outer periphery of the first closing member 32, thereby sealing a gap generated at the engagement place.

The expansion seal 34 may be provided on any of the first annular member 31 and the first closing member 32.

The opening and closing means 33 includes an opening and closing drive unit 35 configured to move the first closing member 32 in the horizontal direction, and a swing drive unit 36 configured to separate the first closing member 32 from the first annular member 31 when the opening and closing drive unit 35 drives.

The opening and closing drive unit 35 includes a straight movement actuator 35a provided on a lower part of the first closing member 32, a guide part 35b disposed below the first closing member 32 and configured to guide the straight movement actuator 35a in the horizontal direction, two guide rollers 35c provided on an upper part of the first closing member 32, and a guide rod 35d integrated with the guide part 35b and configured to guide the guide rollers 35c in the horizontal direction.

The swing drive unit 36 includes a pivotally support part 36a provided on one end side of the guide part 35b and the guide rod 35d, and an electric cylinder 36b provided at the other end part and configured to swing the first closing member 32 together with the guide part 35b and the guide rod 35d.

With this configuration, when an actuation rod of the electric cylinder 36b is extended to move the straight movement actuator 35a in the horizontal direction from a position in the closed state toward the end part at which the electric cylinder 36b is provided while the expansion seal 34 is contracted, the first closing member 32 is separated from the inside portion 31b of the first annular member 31 to open the opening Ob of the first annular member 31 as illustrated in FIG. 4.

When the straight movement actuator 35a is returned to the position in the closed state to contract the actuation rod of the electric cylinder 36b, the first closing member 32 is engaged with the inside portion 31b to close the opening Ob. Thereafter, the expansion seal 34 is expanded to seal the gap generated at the engagement place.

Similarly to the manual incubator 3, the automatic incubator 4 as the second auxiliary aseptic device has the internal space aseptically maintained in environment preferable for cell culture. The automatic incubator 4 includes inside a rack on which a culture container is to be placed, and an automatic housing mechanism configured to automatically place the culture container on the rack. The automatic incubator 4 is movable with a caster 4a.

The housing container 5 as the second auxiliary aseptic device is a bottomed tubular container, and can be directly carried by the worker. The housing container 5 houses a material or the like to be conveyed into the main isolator 2, and also waste or the like generated in the main isolator 2.

As illustrated in FIGS. 5 and 6, the second auxiliary connection part 8 provided on each of the automatic incubator 4 and the housing container 5 as the second auxiliary aseptic devices includes a hollow connection body 40 and a second annular member 41 protruding from the connection body 40.

The inside of the connection body 40 is communicated with the internal space of the automatic incubator 4 or the housing container 5. The inside of the second annular member 41 provided in front serves as an opening Os through which the internal space of the second auxiliary aseptic device is externally opened.

The second annular member 41 can be engaged with the connection opening part Oc of the external blockage member 9. When expanded while the second annular member 41 is engaged with the connection opening part Oc, the expansion seal 28 provided on the connection opening part Oc seals a gap generated where the second annular member 41 inserted into the connection opening part Oc is engaged with the connection opening part Oc.

The internal side of the automatic incubator 4 or the housing container 5 at the opening Os of the second annular member 41 is closed by a second closing member 42 provided in the connection body 40. The second closing member 42 is opened and closed when a rotational shaft 42a provided below the second closing member 42 is driven by a motor (not illustrated).

A sealing member 43 is provided around the opening Os toward the internal space on a wall surface 40a of the connection body 40 on which the second annular member 41 is provided. An outer peripheral rim 42b formed in the second closing member 42 is pressed against the sealing member 43 to seal the opening Os.

The second closing member 42 may be opened and closed by other methods. For example, the second closing member 42 may be driven by operating a handle provided outside the automatic incubator 4 and coupled with a cam mechanism configured to operate simultaneously with the rotational shaft 42a. Alternatively, the second closing member 42 may be constantly pressed in the closing direction by a spring, and when communicated with the main isolator 2, the second closing member 42 may be opened against pressing force of the spring by the worker wearing the glove 11.

The following describes a method of using the isolator system 1 having the above-described configuration. The description is first made on, with reference to FIGS. 3 and 4, an operation when cells are housed in a culture container at the main isolator 2 and then the culture container is moved to the manual incubator 3.

Initially, the manual incubator 3 is separated from the main isolator 2, and the main connection part 6 of the main isolator 2 and the first auxiliary connection part 7 of the manual incubator 3 are closed by the internal opening and closing member 22 and the first closing member 32, respectively.

In this state, the manual incubator 3 is moved to the vicinity of the main isolator 2 by the worker, and thereafter, the main isolator 2 and the manual incubator 3 are connected with each other through the main connection part 6 and the first auxiliary connection part 7.

Specifically, as illustrated in FIG. 3, the first annular member 31 of the first auxiliary connection part 7 provided on the manual incubator 3 is inserted into the tubular member 21 of the main connection part 6 provided on the main isolator 2. Subsequently, the air supply means (not illustrated) expands the expansion seal 27 provided on the tubular member 21.

Accordingly, the expansion seal 27 closely contacts an outer peripheral surface of the first annular member 31 so that the tubular member 21 and the first annular member 31 are connected with each other in an air-tight state, and the connection space S1 partitioned by the internal opening and closing member 22 of the main isolator 2 and the first closing member 32 of the manual incubator 3 is formed inside the tubular member 21 and the first annular member 31.

Right before the sealing, an inner surface of the connection space S1 has been externally exposed. Thus, the supply valve 13a illustrated in FIG. 2 is opened to perform decontamination by supplying decontamination gas into the tubular member 21 through the supply pipe 13A from the decontamination means 13. Thereafter, the discharge valve 13b is opened to perform aeration by circulating aseptic air from the supply pipe 13A to the discharge pipe 13B, thereby discharging the decontamination gas.

When the decontamination of the connection space S1 has ended in this manner, the internal opening and closing member 22 of the main isolator 2 and the first closing member 32 of the manual incubator 3 are opened so that the work space W and the internal space can be communicated with each other while being aseptically maintained.

Then, when the work space W of the main isolator 2 and the internal space of the manual incubator 3 are communicated with each other, the worker wearing the glove 11 of the main isolator 2 places the culture container on the rack in the manual incubator 3.

After a predetermined number of culture containers are housed in the manual incubator 3, the internal opening and closing member 22 of the main isolator 2 and the first closing member 32 of the manual incubator 3 are closed and the expansion seal 27 provided on the tubular member 21 is contracted, thereby canceling the sealing state of the tubular member 21 and the first annular member 31.

Accordingly, the manual incubator 3 can be separated from the main isolator 2. The manual incubator 3 is moved to a culture station (not illustrated) by the truck 3A, and cell culture is performed for a predetermined duration.

The following describes, with reference to FIGS. 5 and 6, work performed when the automatic incubator 4 is connected with the main isolator 2 and a culture container prepared inside the main isolator 2 is housed in the automatic incubator 4.

While the automatic incubator 4 and the main isolator 2 are at separated positions, the main connection part 6 of the main isolator 2 is closed by the internal opening and closing member 22, and the second auxiliary connection part 8 of the automatic incubator 4 is closed by the second closing member 42.

As described above, the automatic incubator 4 includes the second auxiliary connection part 8 smaller than the first auxiliary connection part 7 provided on the manual incubator 3. Accordingly, the second auxiliary connection part 8 cannot be directly connected with the main connection part 6 of the main isolator 2.

Thus, the worker first engages the external blockage member 9 with the outside opening 21b of the tubular member 21 of the main isolator 2, and then expands the expansion seal 27 provided on the tubular member 21 to seal the gap generated at the engagement place.

Subsequently, the worker moves the automatic incubator 4 to the vicinity of the main isolator 2 and inserts the second annular member 41 of the second auxiliary connection part 8 of the automatic incubator 4 into the connection opening part Oc of the external blockage member 9. In this case, positioning is performed by engaging the positioning pin 4a of the automatic incubator 4 with the recess 9c provided in the external blockage member 9.

The worker then connects the air supply hose 29 from the air supply means to the connection port 9d (refer to FIG. 7) provided on the external blockage member 9, and expands the expansion seal 28 provided on the connection opening part Oc.

Accordingly, the expansion seal 28 closely contacts an outer peripheral surface of the second annular member 41, thereby sealing the gap generated where the second annular member 41 and the connection opening part Oc are engaged with each other, and a connection space S2 partitioned by the internal opening and closing member 22 of the main isolator 2 and the second closing member 42 of the automatic incubator 4 is formed inside of the tubular member 21 and the second annular member 41.

Thereafter, similarly to the connection space S1, the connection space S2 is decontaminated by the decontamination means 13. Then, the worker opens the internal opening and closing member 22 of the main isolator 2 and the second closing member 42 of the automatic incubator 4 so that the work space W of the main isolator 2 and the internal space of the automatic incubator 4 are communicated with each other while being aseptically maintained.

In the main isolator 2, when the worker or the robot 12 places a culture container on the placement table 30 provided adjacent to the connection opening part Oc of the external blockage member 9, the automatic housing mechanism provided in the automatic incubator 4 grasps the culture container placed on the placement table 30, and automatically places the culture container on the rack provided in the automatic incubator 4.

When a predetermined number of culture containers are housed in the automatic incubator 4, the internal opening and closing member 22 of the main isolator 2 and the second closing member 42 of the automatic incubator 4 are closed and the expansion seal 28 provided on the connection opening part Oc of the external blockage member 9 is contracted.

Accordingly, the automatic incubator 4 is separated from the main isolator 2 and moved to the culture station (not illustrated) by the caster 4a, and cell culture is performed for a predetermined duration.

It is desirable to reduce the size of an opening part of an incubator as much as possible to maintain the internal space in environment preferable for cell culture. In a case of the manual incubator 3, the worker places a culture container on the rack inside through a glove operation. Thus, the opening Ob needs to be formed in a size with operability taken into account.

The opening Os of the automatic incubator 4 only needs to have a size that allows conveyance of a culture container, and thus is formed to be smaller than the opening Ob of the manual incubator 3. Accordingly, the second auxiliary connection part 8 provided on the automatic incubator 4 can be smaller than the first auxiliary connection part 7 provided on the manual incubator 3.

The housing container 5 is provided with the second auxiliary connection part 8. Thus, the housing container 5 can be connected with the main isolator 2 through work same as the work of connecting the automatic incubator 4 so that the work space W of the main isolator 2 and the internal space of the housing container 5 are communicated with each other while being aseptically maintained. The housing container 5 can be separated from the main isolator 2.

The housing container 5 is used as follows: the housing container 5 houses a material or the like to be conveyed into the main isolator 2, and then is communicated with the work space W of the main isolator 2 to convey the material or the like into the work space W; or the empty housing container 5 is communicated with the work space W of the main isolator 2 to house waste or the like generated at the work space W.

As described above, according to the present embodiment, the main connection part 6 provided on the main isolator 2 can be directly connected with the first auxiliary connection part 7 of the manual incubator 3, or can be connected with, in place of the manual incubator 3, the automatic incubator 4 or the housing container 5 provided with the second auxiliary connection part 8 smaller than the first auxiliary connection part 7. Accordingly, the main isolator 2 can be selectively connected with these incubator and container.

In other words, the single main connection part 6 of the main isolator 2 can be connected with auxiliary aseptic devices provided with the first and second auxiliary connection part 7 and 8 having sizes different from each other. This eliminates the need to have a space in which a plurality of main connection parts are provided for connection with a plurality of kinds of auxiliary aseptic devices, thereby preventing increase in the size of the main isolator 2.

In the above-described embodiment, the main isolator 2 includes the single main connection part 6 but is not limited thereto. The main isolator 2 may include a plurality of main connection parts 6 so that, for example, the main isolator 2 can be simultaneously connected with the manual incubator 3 and the housing container 5.

In the above-described embodiment, the automatic incubator 4 and the housing container 5 as the second auxiliary aseptic devices each include the same second auxiliary connection part 8, but the size of the second auxiliary connection part 8 may be different between the automatic incubator 4 and the housing container 5.

In this case, the external blockage member 9 may include a plurality of connection opening parts Oc corresponding to the second auxiliary connection parts 8 having different sizes, or a plurality of external blockage members 9 in each of which a single connection opening part Oc is formed may be provided.

Alternatively, the single external blockage member 9 may include a plurality of second auxiliary connection parts 8 having identical sizes. However, when a plurality of connection opening parts Oc are formed in the single external blockage member 9, a closing member configured to close any unused connection opening part Oc needs to be provided.

REFERENCE SIGNS LIST 1 isolator system
2 main isolator (main aseptic device)
3 manual incubator (first auxiliary aseptic device)
automatic incubator (second auxiliary aseptic device)
5 housing container (second auxiliary aseptic device)
6 main connection part
7 first auxiliary connection part
8 second auxiliary connection part
9 external blockage member
21 tubular member
21a internal opening
21b outside opening
22 internal opening and closing member 28 expansion seal (sealing means)
31 first annular member
32 first closing member
41 second annular member
42 second closing member
O, Ob, Os opening
Oc connection opening part
W work space

What is claimed is:

1. An aseptic work system in which a main aseptic device including inside an aseptically maintained work space is detachably provided with auxiliary aseptic devices each including an aseptically maintained internal space, and the work space of the main aseptic device and the internal spaces of the auxiliary aseptic devices are capable of being communicated with each other while being aseptically maintained, characterized in that the main aseptic device includes a main connection part having an opening through which the work space is externally opened, and an internal opening and closing member configured to open and close the opening of the main connection part in the work space, the auxiliary aseptic devices are a first auxiliary aseptic device including a first auxiliary connection part connectable with the main connection part of the main aseptic device, and a second auxiliary aseptic device including a second auxiliary connection part smaller than the first auxiliary connection part, and an external blockage member configured to externally block the opening of the main connection part is provided, and the external blockage member includes a connection opening part to which the second auxiliary connection part is connectable.

2. The aseptic work system according to claim 1, characterized in that the opening of the main connection part is formed of a tubular member, and a decontamination means configured to supply a decontamination medium into the tubular member is provided.

3. The aseptic work system according to claim 1, characterized in that the first auxiliary connection part and the second auxiliary connection part have openings through which the internal spaces of the respective auxiliary aseptic devices are externally opened, and include a first closing member and a second closing member, respectively, that are configured to close the openings.

4. The aseptic work system according to claim 1, characterized in that the second auxiliary connection part has an opening through which the internal space of the second auxiliary aseptic device is externally opened, and includes an annular member surrounding the opening and configured to be engaged with the connection opening part of the external blockage member, and a sealing means configured to seal a gap generated where the annular member is engaged with the connection opening part.

5. The aseptic work system according to claim 1, characterized in that the external blockage member is provided with a plurality of connection opening parts.

6. The aseptic work system according to claim 1, characterized in that the first auxiliary aseptic device and the second auxiliary aseptic device are incubators.

7. The aseptic work system according to claim 1, characterized in that at least one of the first auxiliary aseptic device and the second auxiliary aseptic device is a housing container in which an object is housed.

* * * * *